United States Patent
Wajc et al.

(10) Patent No.: US 8,383,835 B2
(45) Date of Patent: Feb. 26, 2013

(54) PROCESS FOR THE PRODUCTION OF CYCLIC DIESTERS OF ALPHA-HYDROXYACIDS

(75) Inventors: Samuel J. Wajc, Haifa (IL); Henri Wautier, Braine le Comte (BE)

(73) Assignee: Ktanton Ltd., Haifa (IL)

( * ) Notice: Subject to any disclaimer, the term of this patent is extended or adjusted under 35 U.S.C. 154(b) by 181 days.

(21) Appl. No.: 12/747,932

(22) PCT Filed: Dec. 23, 2008

(86) PCT No.: PCT/EP2008/068272
§ 371 (c)(1),
(2), (4) Date: Jun. 14, 2010

(87) PCT Pub. No.: WO2009/080834
PCT Pub. Date: Jul. 2, 2009

(65) Prior Publication Data
US 2010/0267970 A1    Oct. 21, 2010

Related U.S. Application Data

(60) Provisional application No. 61/008,654, filed on Dec. 26, 2007.

(51) Int. Cl.
*C07D 319/00* (2006.01)
(52) U.S. Cl. ....................................................... 549/274
(58) Field of Classification Search ................... 549/274
See application file for complete search history.

(56) References Cited

U.S. PATENT DOCUMENTS

| | | | |
|---|---|---|---|
| 3,429,777 | A | 2/1969 | Bode |
| 5,319,107 | A | 6/1994 | Benecke et al. |
| 5,357,035 | A | 10/1994 | Gruber et al. |
| 5,766,439 | A | 6/1998 | Eyal et al. |
| 2005/0281913 | A1 | 12/2005 | Krieken et al. |
| 2006/0014975 | A1 | 1/2006 | Coszach et al. |
| 2009/0318713 | A1 | 12/2009 | Wajc |
| 2010/0113806 | A1 | 5/2010 | Wajc |

FOREIGN PATENT DOCUMENTS

WO   WO2008/071776 A2   6/2008

OTHER PUBLICATIONS

Drumright et al. Adv. Mater. 2000, 12, No. 23, 1841-1846, p. 1841, shceme on col. B.*
Drumright et al. Adv. Mater. 2000, 12, No. 23, 1841-1846.*
U.S. Appl. No. 12/518,972, filed Nov. 2, 2009, Wajc.
U.S. Appl. No. 12/483,309, filed Jun. 12, 2009, Wajc.
Ray E. Drumright et al—"Polylactic acid technology"—Adv. Mater. 2000, vol. 12 (23), pp. 1841-1846 (6 pgs.).
Rathin Data et al—"Technological and Economic potential of poly(lactic acid) and lactic acid derivatives"—FEMS Microbiology Reviews vol. 16, (1995), pp. 221-231 (11 pgs.).
Toru Motoyama et al.—"Effects of MgO catalyst on depolymerization of poly-L-lactic acid to L,L-lactide"—Polymer Degradation and Stability (2007), vol. 92, pp. 1350-1358 (9 pgs.).
Yukon Sakata et al.—"Characterization of dehydration and hydration behavior of calcium lactate pentahydrate and its anhydrate"—Colloids and Surfaces B: Biointerfaces (2005) vol. 46, pp. 135-141 (7 pgs.).
Bezzi et al.—"I prodotti di anidrificazione dell'acido lattico come tipo delle trasformazioni degli esteri ciclici in poliesteri lineari [The products of anhydridification of lactic acid as type of the transformation of cyclic esters into linear polyesters]"—Mem reale accad Italia, Classe sci. fis., mat. nat. (1937) vol. 8, pp. 127-213—in Italian—including CAS abstract in English language (88 pgs).
Mao Yin & Gregory L. Baker—"Preparation and Characterization of substituted polylactides"—Macromolecules (1999) vol. 32(23), pp. 7711-7717 (8 pgs.).

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

Process for the synthesis of a cyclic diester of an alpha-hydroxyacid, comprising the following steps:
- an alkalino-earth salt of the corresponding alpha-hydroxyacid is mixed with said alpha-hydroxyacid and water;
- the mixture is treated by evaporation-crystallization, so that a hydrate of the alkalino-earth salt of the linear dimer of the corresponding alpha-hydroxyacid precipitates;
- the hydrated salt is dehydrated to give the corresponding anhydrous salt; and
- the anhydrous salt is pyrolyzed, releasing the cyclic diester of the corresponding alpha-hydroxyacid and leaving the alkalino-earth hydroxide as solid residue.

11 Claims, 1 Drawing Sheet

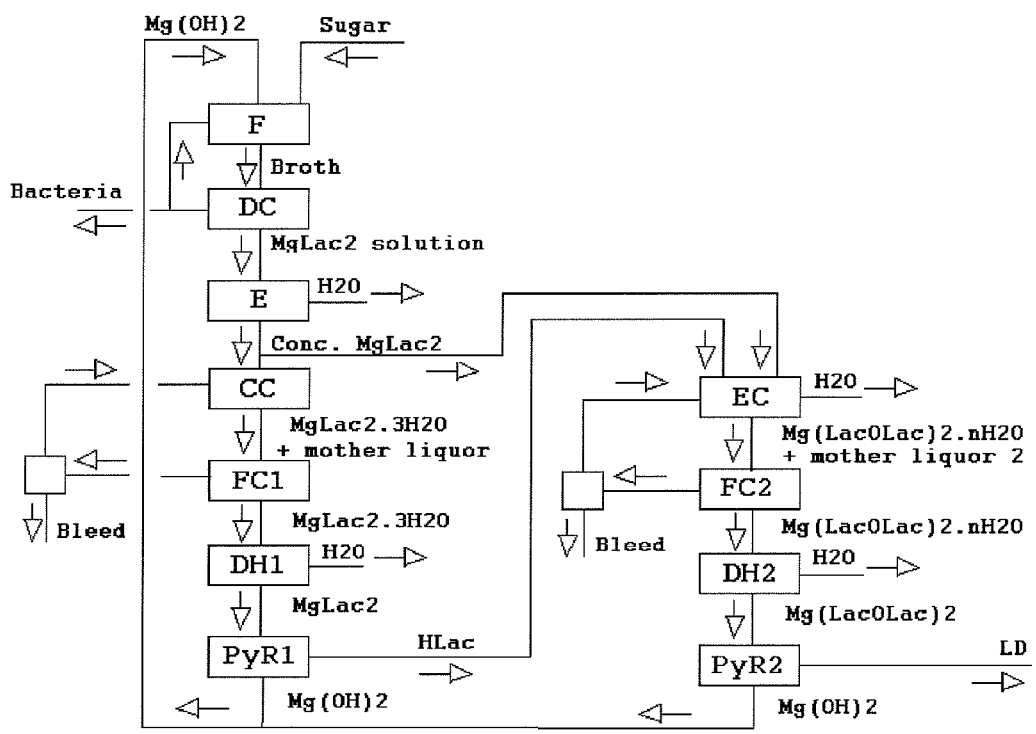

PROCESS FOR THE PRODUCTION OF CYCLIC DIESTERS OF ALPHA-HYDROXYACIDS

CROSS-REFERENCE TO RELATED APPLICATIONS

This application is a U.S. national stage application under 35 U.S.C. §371 of International Application No. PCT/EP2008/068272 filed Dec. 23, 2008, which claims priority to U.S. Provisional Application No. 61/008,654 filed Dec. 26, 2007, the whole content of this application being incorporated herein by reference.

BACKGROUND OF THE INVENTION

Most reported syntheses of Polylactic Acid (PLA) use enantiomerically pure Lactic Acid (LA) as raw material. As the raw material for the synthesis of LA is renewable, the commercial production of that biodegradable polymer is slowly gaining ground (Drumright et al., "Polylactic Acid Technology", 2000, Adv. Mater., v. 12, pp. 1841-1846).

Its applications in the medical field may well command a high price, but if it is to compete successfully with fossil fuel derived polymers such as Polystyrene (whose mechanical properties are quite similar to those of PLA) or Polyethylene Terephtalate (for bottles), then its production cost has to decrease.

The synthesis reaction of PLA is a ring-opening polymerization of Lactide (LD) in the presence of a homogeneous catalyst (U.S. Pat. No. 5,319,107). The reaction conditions are now well known and there is apparently little to be gained by way of better product quality or smaller energy consumption in this step.

On the contrary, the classical production process from LA of the key intermediate, the cyclic diester LD is fraught with difficulties.

Several steps in the classical process are essentially single step evaporations (under low pressure) meant to remove solution water or condensation reaction water, as appears from the following description:

a.—Fermentation of a well-chosen carbohydrate by well-chosen bacteria, in the presence of $Ca(OH)_2$ (or $CaCO_3$) leads to the production of a suspension of bacteria in a solution of Calcium Lactate ($CaLac_2$).

b.—the bacteria are separated by centrifugation or filtration and discarded (U.S. Pat. No. 5,766,439)

c.—the filtrate reacts with Sulfuric Acid, which causes the precipitation of Gypsum (Calcium Sulfate Dihydrate) and the liberation of Lactic Acid (LA) as a solution of some 10% by weight. (US Pat. Appl. No. 20050281913)

d.—that solution is concentrated by distillation to 85-88% LA by weight.

e.—the concentrated LA solution, in the presence of a homogeneous catalyst, undergoes a prepolymerization in a vacuum distillation column, where more water is separated.

f.—as the molecular weight of the prepolymer is only about 1000, its mechanical properties are not suitable for industrial use.

g.—the prepolymer is then depolymerized by back-biting in the presence of a well-chosen catalyst under vacuum and the LD leaving the reactor in the vapor phase is condensed as a liquid or directly fed to a distillation column to produce liquid crude LD (mixed with LA, some of its light oligomers, water, unwanted enantiomers of LD, etc. . . . ) (U.S. Pat. No. 5,357,035).

h.—the crude LD is further purified by liquid-liquid extraction with water followed by crystallization from aqueous solution (US Pat. Appl. No. 20060014975).

i.—centrifugation gives a cake of purified LD, but since the impurity level is still too large, a last operation is required:

j.—melt crystallization with sweating to remove the impurities by gravity flow.

All these operations are well known, so that it is possible to produce for instance the enantiomer L-LD with a purity of up to 99.9%. But the yield of some of the operations of this long chain is rather modest, so that large recycle flows are required, so that the various equipment items tend to be large with large energy requirements.

A large Research and Development effort has been devoted to the improvement of the classical LD production process, i.e. the process where Lactic Acid is considered as the raw material (Rathin Datta, "Technological and economic potential of poly(lactic acid) and lactic acid derivatives", 1995, FEMS Microbiology Reviews, v. 16, pp. 221-231). For instance, liquid-liquid extraction processes may offer an energetically less demanding way than water evaporation for the LA concentration, but complete elimination of traces of the solvent remains a problem. More advanced separation techniques, such as electrodialysis of ethyl lactate, are promising.

In the classical process, a large amount of waste product (Calcium Sulfate Dihydrate, or gypsum) is produced.

Other alpha-hydroxyacids, such as Glycolic Acid (GA), may similarly be dimerized to the corresponding cyclic diester and thence to the polyacid (e.g. glycolide leading to Polyglycolic Acid, PGA) by the same process and with the same disadvantages.

Notwithstanding these handicaps, PLA (and PGA) may well become a commodity product, so that the question of disposal or recycling of large quantities of waste material, such as empty bottles, must be addressed. A possibility is to depolymerize by heating at around 300° C., produce LD vapor and condense it. The process is very simple, but racemization at such a high temperature degrades the enantiomeric purity of the product. In order to by-pass this last difficulty, one may mix CaO or MgO powder to PLA and depolymerize by pyrolysis at lower temperature (Toru Motoyama, "Effects of MgO catalyst on depolymerization of poly-L-lactic acid to L,L-lactide", 2007, Polymer Degradation and Stability, v. 92, pp. 1350-1358).

Especially relevant to the present invention is the observation that the depolymerization temperature (and the extent of racemization) of PLA with a molecular weight of 170 000 regularly decreases when the size of the MgO particles decreases (FIGS. 2 and 3 in Toru Motoyama, 2007). Also noteworthy is the fact that in said reference the MgO weight represents 5% (as Mg) of the weight of PLA.

Another point of interest in the former art is that Magnesium Hydroxide ($Mg(OH)_2$) will dehydrate only at a much higher temperature (around 400° C.).

Yet another point of interest in the former art is that the linear dimer of LA, namely Lactoyllactic Acid (LacOLacA) is a stronger acid than LA (Bezzi, S., "I produtti di anidrificazione dell'acido lattico come tipo delle trasformazioni degli esteri ciclici in poliesteri lineari", 1937, Mem. reale acad. Italia, Classe sci. fis., mat. e nat., v. 8, pp. 127-213).

It has long been known that the production of Magnesium Lactate ($MgLac_2$) by fermentation is as easy as that of $CaLac_2$ (U.S. Pat. No. 3,429,777). Moreover, since the solubility of MgLac$_2$ is somewhat larger than that of CaLac$_2$, the former may have an advantage if the Lactate is to be separated by crystallization.

If it were possible to go directly from the LA raw material, i.e. Calcium or Magnesium Lactate, directly to the LD, there would be no question of remaining traces of extraction solvent, nor of traces of depolymerization catalyst, and the production cost of PLA would probably decrease.

In a former patent application (Provisional Pat. Appl. 60/874,475), I have disclosed a process that would achieve these aims by bringing to the LD production reactor anhydrous reactants, such as Anhydrous Calcium Lactate and Sulfuric Anhydride, such that the organic product would have been dehydrated in a former operation under mild conditions.

The waste product obtained in said process may be used industrially, but a process without waste products would be even more attractive. Such a waste-less process is the object of the present invention.

BRIEF SUMMARY OF THE INVENTION

The present invention relates to a process for the synthesis of a cyclic diester of an alpha-hydroxyacid, comprising the following steps:
  an alkalino-earth salt of the corresponding alpha-hydroxyacid is mixed with said alpha-hydroxyacid and water;
  the mixture is treated by evaporation-crystallization, so that a hydrate of the alkalino-earth salt of the linear dimer of the corresponding alpha-hydroxyacid precipitates;
  the hydrated salt is dehydrated to give the corresponding anhydrous salt; and.
  the anhydrous salt is pyrolyzed (preferably in the presence of water vapor or an inert carrier), releasing the cyclic diester of the corresponding alpha-hydroxyacid and leaving the alkalino-earth hydroxide as solid residue.

This residue may in turn be used in a process where the alkalino-earth salt of the alpha-hydroxyacid is produced by fermentation of sugar (preferably natural sugars coming from fruits, plants, dairy products . . . ) in the presence of bacteria. It is namely so that such fermentation processes require a basic pH so that an alkalino-earth hydroxide is generally added to the reaction medium.

The alpha-hydroxyacid of the process according to the invention may hence be any such acid obtainable by fermentation like lactic acid, glycolic acid, glutaric acid, mandelic acid, malic acid, citric acid or tartaric acid, the first two being preferred. The invention gives good results with lactic acid.

As to the alkalino-earth metal, it is preferably chosen between Mg, Ca, Zn, Al and Fe, the first two being preferred.

alkalino-earth salts of alpha-hydroxyacids are generally available commercially under a hydrated form. For instance, Mg lactate dihydrate is available under the commercial denomination PURAMEX® MG.

Alpha-hydroxyacids usable in the process of the invention are also available commercially; for instance, a 80% lactic acid aqueous solution is available under the commercial denomination PURAC FCC80.

Instead of using a commercial alpha-hydroxyacid, according to an embodiment of the present invention, said alpha-hydroxyacid is obtained by pyrolysis of an alkalino-earth salt of said alpha-hydroxyacid in the presence of water. In a preferred embodiment, where the process of the invention is combined with a fermentation process as described above, half of the final reaction medium (hence containing the alkalino-earth salt of the alpha-hydroxyacid) is subjected to pyrolysis in the presence of water to give the corresponding alpha-hydroxyacid (generally in vapor form) and alkalino-earth hydroxide.

Hence, the present invention also relates to a process for the synthesis of cyclic diesters of alpha-hydroxyacids, where the only main reactant is an aqueous solution of an alkalino-earth salt of the corresponding alpha-hydroxyacid.

In this process, the solution is preferably first concentrated by evaporation Then preferably about one half of said concentrated solution is cooled, so that a hydrate of the alkalino-earth salt of the corresponding alpha-hydroxyacid precipitates.

The hydrated salt is then preferably separated from the mother-liquor, and further dehydrated to give the corresponding anhydrous salt.

The obtained anhydrous salt is preferably pyrolyzed at mild temperature (typically, at 250° C. or less) in the presence of water vapor, releasing the alpha-hydroxyacid as vapor and leaving the alkalino-earth hydroxide as solid residue.

The alpha-hydroxyacid vapor can be absorbed in the second half of the concentrated solution, and treated by evaporation-crystallization, so that a hydrate of the alkalino-earth salt of the linear dimer of the corresponding alpha-hydroxyacid precipitates. This hydrated salt may then separated from its mother-liquor, and further dehydrated to give the corresponding anhydrous salt.

This salt is then advantageously pyrolyzed at mild temperature (350° C. or less), preferably in the presence of water vapor or an inert carrier, releasing the cyclic diester of the corresponding alpha-hydroxyacid as vapor and leaving the alkalino-earth hydroxide as solid residue.

This alkalino-earth hydroxide may then be recycled to a fermentor or to an alpha-hydroxyacid neutralization reactor.

In this embodiment, the vapor of cyclic diester of alpha-hydroxyacid is selectively desublimated (condensed) and purified in situ by sweating, the impurities being mainly removed by evaporation.

For diesters whose volatility is too low, this separation step may be replaced by liquid-solid extraction step(s), followed by crystallization from solution.

This preferred embodiment will be illustrated below is a specific case by way of example.

The raw material for the production of LD is a Magnesium Lactate solution, produced, for instance, by fermentation of sugar in the presence of Magnesium Hydroxide, adapted bacteria and nutrients for said bacteria. The bacteria in the broth leaving the fermentor are separated, for instance by centrifugation, and the resulting liquid concentrated to give a concentrated solution of Magnesium Lactate. This solution is split in two equal streams for further treatment.

One half of this Magnesium Lactate solution is submitted to cooling crystallization in order to precipitate a hydrate (for instance Magnesium Lactate Trihydrate). This hydrated salt is dehydrated at atmospheric pressure, leading to Magnesium Lactate Anhydrate. The latter is pyrolyzed in the presence of Water vapor at mild temperature (below 250° C.) and releases LA vapor, leaving a solid residue of Mg(OH)$_2$.

The LA vapor produced in the former step is condensed in the second half of the Magnesium Lactate solution. Controlled evaporation-crystallization of this mixture leads to formation in solution of Lactoyllacte ions and to precipitation of hydrated Magnesium Lactoyllacte crystals. This hydrated salt is dehydrated at atmospheric pressure, leading to Magnesium Lactoyllactate Anhydrate. The latter is pyrolyzed, preferably in the presence of Water vapor or an inert carrier, and at a somewhat higher temperature (but below 350° C. to avoid racemization), and releases LD vapor, leaving a solid residue of $Mg(OH)_2$. Any available commercial source of pure Lactic Acid could obviously also be used to produce Magnesium Lactoyllactate, using all the Magnesium Lactate produced by fermentation.

BRIEF DESCRIPTION OF THE DRAWING

FIG. 1 is a diagram of a process for the production of cyclic diesters of alpha-hydroxyacids.

DETAILED DESCRIPTION OF THE INVENTION

A specific embodiment of the process of the invention will now be described by reference to the annexed drawing.

The first two steps are classical:

A.—Fermentation (fermentor F at upper left corner of the drawing) of a well-chosen carbohydrate in the presence of $Mg(OH)_2$ leads to the production of a suspension of bacteria in a solution of Magnesium Lactate ($MgLac_2$).

B.—The bacteria are separated by centrifugation (decanter-centrifuge DC) or filtration and discarded The next step is similar to that disclosed in U.S. Pat. No. 5,766,439:

C.—The filtrate (or centrate), a solution of Magnesium Lactate, is concentrated by evaporation of water (evaporator E).

In the first column, one half of this concentrated solution is further treated as disclosed in U.S. Pat. No. 5,766,439, in the following two steps:

D.—Cooling crystallization (apparatus CC) brings about separation of a hydrate of Magnesium Lactate (the trihydrate if the crystallization temperature is low enough)

E.—Separation of these crystals by centrifugation (filter-centrifuge $FC_1$); further treatment of the mother-liquor for separation of more $MgLac_2$ trihydrate ($MgLac_2$ TH) and separation of a bleed solution.

The following steps embody the gist of the present invention:

F.—Slow dehydration (drying oven DH1) of the trihydrate at atmospheric pressure and at a temperature smaller than 150° C. to obtain anhydrous $MgLac_2$ (for the similar case of $CaLac_2$, see Yukoho Sakata et al., "Characterization of dehydration and hydration behavior of calcium lactate pentahydrate and its anhydrate", 2005, Colloids and Surfaces B: Biointerfaces, v. 46, pp. 135-141).

G.—Pyrolysis in the presence of Water vapor of the anhydrous $MgLac_2$ (reactor PyR1) at a temperature (less than 250° C.) high enough for the production of LA vapor and low enough to prevent the decomposition of the residual $Mg(OH)_2$. If commercial Lactic Acid of sufficient purity is available, it may be used for the following steps instead of that produced as described here.

In parallel,

H.—Absorption of the produced LA vapor in the remaining half of the concentrated $MgLac_2$ solution produced in evaporator E, followed by condensation reaction and crystallization (in evaporator-crystallizer EC) of a hydrated Magnesium Lactoyllactate ($MgLacOLac_2.nH_2O$).

I.—Separation of the crystals by centrifugation (filter-centrifuge $FC_2$); further treatment of the mother-liquor 2 for separation of more hydrated $MgLacOLac_2$ and separation of a bleed solution.

J.—Dehydration (drying oven $DH_2$) of the hydrated Magnesium Lactoyllactate at atmospheric pressure to obtain anhydrous Magnesium Lactoyllactate ($MgLacOLac_2$).

K.—Pyrolysis, preferably in the presence of Water vapor or an inert carrier, of the anhydrous $MgLacOLac_2$ (reactor $PyR_2$) at a temperature (smaller than 350° C.) high enough for the production of LD vapor and low enough to prevent the decomposition of the residual $Mg(OH)_2$. This is similar to the pyrolysis of PLA (Toru Motoyama, 2007), with a ratio of Mg to Lactate close to 5% (8.3%), and with the ultimate degree of dispersion possible for the Mg.

The last three steps are borrowed from US Pat. Prov. Appl. 60/874,475 (the content of which is incorporated by reference into the present application):

L.—Selective desublimation of LD as a cylindrical solid layer on the vertical tubes of a heat exchanger, under strict temperature control M.—Reheating this layer in order to induce "sweating" so that an impure viscous solution will be produced, but as opposed to what happens in melt crystallizers, the impurities will be evacuated by selective sublimation and not by gravity.

N.—The last step is similar to that in melt crystallization, i.e. evacuation of the purified crystals by complete melting of the layer.

The solid residue in both arms of the process is $Mg(OH)_2$. This is recycled to the fermentor, so that, besides the excess of bacteria and the impurities separated from the mother liquors of the two filter-centrifuges $FC_1$ and $FC_2$, this process leaves no solid waste.

The main thermal energy demand is for the evaporator E. In view of the mild boiling point elevation in Magnesium Lactate solutions, it will be possible to use a multiple-effect evaporator, which will limit the cost of energy (but increase the investment cost).

It will be apparent to those skilled in the art that elimination of most of the water under mild conditions, either by multiple-effect evaporation or by dehydration, rather than by vacuum distillations as is traditionally practiced, is economically commendable. Moreover, during pyrolysis, as soon as LA (in $PyR_1$) or LD (in $PyR_2$) are produced, they are vaporized, so that there is little opportunity for these viscous liquids (the melting points of LA and LD are, respectively 42 and 98° C.) to produce large agglomerates of the Magnesium Hydroxide powder prevalent in each reactor.

It will also be apparent to those skilled in the art that the synthesis by the present process of Glycolide (GD) from GA not produced by fermentation is possible: in a first step, one would react GA solution with reactive Magnesium Hydroxide, obtain a solution of Magnesium Glycolate and copy the rest of the present description from step B hereabove.

It will be apparent to those skilled in the art that less volatile cyclic diesters, such as Mandelide, could still be produced by a variant of the process described hereabove. Indeed, if separation by distillation and desublimation from the corresponding anhydrates of the hydroxyacid on the one hand, and of the cyclic diester on the other hand, is not economically practical, it may still be possible to extract them (solid-liquid extraction) by a suitable solvent, such as toluene, at a temperature close to the hydroxyacid and the diester melting points, respectively. This would be followed by crystallization from solution, separation by centrifugation, and drying of the cake.

Another specific embodiment of the present invention will be described in detail through the Example below.

EXAMPLE 1

Preparation and Pyrolysis of Magnesium Lactoyllactate

Magnesium Lactate Dihydrate (PURAMEX® MG) was dehydrated at atmospheric pressure at 185° C. during 4 hours.

20.2 g of the resulting Anhydrate was thoroughly mixed (mortar) with 22.5 g of 80% Lactic Acid (PURAC FCC80). The homogeneous and fairly fluid mixture was left to react at 110° C. for 2.5 hours, which resulted in complete solidification.

22.82 g of that solid were introduced in the boiler of a BÜCHI Glass Oven B-585 and heated under atmospheric pressure to 100° C. (1 hour), 120° C. (1 hour), 160° C. (40 minutes), and then under 6 mbar at 160° C. (1 hour). Two fractions of condensate were collected in two separate vessels in line with the boiler, that in the vessel closest to the boiler being 1.51 g of a transparent oily liquid (F1) that was analyzed by RMN, while that collected in the last vessel (4.37 g) was assumed to be essentially water and was not analyzed.

The condensate collection vessels were replaced by clean ones and distillation under 6 mbar went on for 2.7 hours, while the set point of the boiler slowly increased from 170° C. to 280° C.

2.19 g of solids (F2) were collected and analyzed by RMN.

The white solid residue in the boiler amounted to 10.09 g (a weight loss of 10.73 g having hence taken place).

The analytical results (% by weight) collected were as follows:

F1: 3% LD, 7% dimer of lactic acid (LA), 90% LA
F2: 88% LD, 5% LA dimer, 7% LA

These analytical results could be interpreted as follows:

a.—Magnesium Lactoyllactate Dihydrate was produced under atmospheric pressure up to 160° C. by reaction between the Anhydrate and the Water brought in with the Lactic Acid.

b.—Decreasing the pressure to 6 mbar at 160° C. resulted in the distillation of free water.

c.—Progressively increasing the temperature to 280° C. under vacuum led to the dehydration of the Hydrated Magnesium Lactoyllactate and to the its decomposition in Magnesium Hydroxide and Lactide, the former remaining in the boiler and the latter being condensed in F2 mainly.

The invention claimed is:

1. A process for the synthesis of a cyclic diester of an alpha-hydroxyacid, comprising the following steps:
mixing magnesium salt of the corresponding alpha-hydroxyacid with said alpha-hydroxyacid and water;
treating the mixture by evaporation-crystallization, so that a hydrate of the magnesium salt of the linear dimer of the corresponding alpha-hydroxyacid precipitates;
dehydrating the hydrated salt to give the corresponding anhydrous salt; and
pyrolyzing the anhydrous salt, releasing the cyclic diester of the corresponding alpha-hydroxyacid and leaving the magnesium hydroxide as solid residue.

2. The process according to claim 1, wherein the magnesium hydroxide is added to a reaction medium comprising sugar and bacteria so that a solution comprising the corresponding magnesium salt of the alpha-hydroxyacid is produced by fermentation.

3. The process according to claim 1, wherein the alpha-hydroxyacid is selected from the group consisting of lactic acid, glycolic acid, glutaric acid, mandelic acid, malic acid, citric acid, and tartaric acid.

4. The process according to claim 2, wherein the solution comprising the magnesium salt of the alpha-hydroxyacid is concentrated by evaporation.

5. The process according to claim 4, wherein one half of said concentrated solution is cooled, so that a hydrate of the magnesium salt of the corresponding alpha-hydroxyacid precipitates.

6. The process according to claim 1, wherein said hydrated salt is separated from its mother-liquor, and is further dehydrated to give the corresponding anhydrous salt.

7. The process according to claim 1, wherein said anhydrous salt is pyrolyzed at mild temperature in the presence of water vapor, releasing the alpha-hydroxyacid and leaving the magnesium hydroxide as solid residue.

8. The process according to claim 5,
wherein said alpha-hydroxyacid is in vapor form, is absorbed in the second half of the concentrated solution, and is treated by evaporation-crystallization, so that a hydrate of the magnesium salt of the linear dimer of the corresponding alpha-hydroxyacid precipitates;
wherein the hydrated salt is separated from its mother-liquor, and is further dehydrated to give the corresponding anhydrous salt;
wherein the anhydrous salt is pyrolyzed at mild temperature, releasing the cyclic diester of the corresponding alpha-hydroxyacid as vapor and leaving the magnesium hydroxide as solid residue.

9. The process according to claim 8, wherein the magnesium hydroxide is recycled to a fermentor or to an alpha-hydroxyacid neutralization reactor.

10. The process according to claim 8, wherein the vapor of cyclic diester of alpha-hydroxyacid is condensed and purified in situ by sweating, the impurities being mainly removed by evaporation.

11. The process according to any of claim 5,
wherein said alpha-hydroxyacid is in liquid or solid form, is separated from the solid residue by distillation or liquid extraction and then is reacted with the second half of the concentrated solution, and is treated by evaporation-crystallization, so that a hydrate of the magnesium salt of the linear dimer of the corresponding alpha-hydroxyacid precipitates;
wherein the hydrated salt is separated from its mother-liquor, and is further dehydrated to give the corresponding anhydrous salt;
wherein the anhydrous salt is pyrolyzed at mild temperature, to give the cyclic diester of the corresponding alpha-hydroxyacid as a solid or a liquid entrapped in the magnesium hydroxide as solid residue; and
wherein said diester is separated from the solid residue by one or more liquid-solid extraction steps, followed by a distillation or a crystallization from solution.

* * * * *